United States Patent
Bharat et al.

(10) Patent No.: US 10,265,543 B2
(45) Date of Patent: Apr. 23, 2019

(54) BEAM SEGMENT-LEVEL DOSE COMPUTATION AND TEMPORAL MOTION TRACKING FOR ADAPTIVE TREATMENT PLANNING

(71) Applicant: KONINKLIJKE PHILIPS N.V., Eindhoven (NL)

(72) Inventors: Shyam Bharat, Ossining, NY (US); Mingyao Zhu, Manchester, MO (US); Parag Jitendra Parikh, Webster Groves, MO (US); Karl Antonin Bzdusek, Madison, WI (US)

(73) Assignees: KONINKLIJKE PHILIPS N.V., Eindhoven (NL); WASHINGTON UNIVERSITY, St. Louis, MS (US)

( * ) Notice: Subject to any disclaimer, the term of this patent is extended or adjusted under 35 U.S.C. 154(b) by 725 days.

(21) Appl. No.: 14/358,072

(22) PCT Filed: Nov. 30, 2012

(86) PCT No.: PCT/IB2012/056867
§ 371 (c)(1),
(2) Date: May 14, 2014

(87) PCT Pub. No.: WO2013/080175
PCT Pub. Date: Jun. 6, 2013

(65) Prior Publication Data
US 2014/0336438 A1    Nov. 13, 2014

Related U.S. Application Data

(60) Provisional application No. 61/564,885, filed on Nov. 30, 2011.

(51) Int. Cl.
*A61N 5/10* (2006.01)
*A61B 18/00* (2006.01)
*A61N 7/02* (2006.01)

(52) U.S. Cl.
CPC ............ *A61N 5/1031* (2013.01); *A61B 18/00* (2013.01); *A61N 5/1037* (2013.01);
(Continued)

(58) Field of Classification Search
CPC .... A61N 5/103; A61N 5/1031; A61N 5/1307; A61N 5/1039; A61N 5/1049
(Continued)

(56) References Cited

U.S. PATENT DOCUMENTS

| | | |
|---|---|---|
| 5,538,494 A | 7/1996 | Matsuda |
| 6,731,970 B2 | 5/2004 | Schlossbauer et al. |

(Continued)

FOREIGN PATENT DOCUMENTS

| | | |
|---|---|---|
| EP | 2108401 A1 | 10/2009 |
| JP | 2011502010 | 1/2011 |
| WO | 2010109345 A1 | 9/2010 |

OTHER PUBLICATIONS

Hugo, G. D., et al.; Population and patient-specific target margins for 4D adaptive radiotherapy to account for intra- and inter-fraction variation in lung tumour position; 2007; Phys. Med. Biol.; 52:257-274.

*Primary Examiner* — Samuel G Gilbert (57) ABSTRACT

A treatment planning system for generating patient-specific treatment. The system including one or more processors programmed to receive a radiation treatment plan (RTP) for irradiating a target over the course of one or more treatment fractions, said RTP including a planned dose distribution to be delivered to the target, receive motion data for at least one of the treatment fractions of the RTP, receive temporal delivery metric data for at least one of the treatment fractions of the RTP, calculate a motion-compensated dose distribution for the target using the motion data and the temporal delivery metric data to adjust the planned dose distribution based on the received motion data and temporal delivery metric data, and compare the motion-compensated dose distribution to the planned dose distribution.

18 Claims, 2 Drawing Sheets

(52) U.S. Cl.
CPC ......... *A61N 5/1039* (2013.01); *A61N 5/1064* (2013.01); *A61N 5/1071* (2013.01); *A61N 5/1077* (2013.01); *A61N 7/02* (2013.01); *A61N 5/1047* (2013.01); *A61N 2005/1087* (2013.01)

(58) Field of Classification Search
USPC .............................................. 600/1; 378/65
See application file for complete search history.

(56) References Cited

U.S. PATENT DOCUMENTS

| | | | |
|---|---|---|---|
| 7,643,661 B2* | 1/2010 | Ruchala | A61N 5/103 |
| | | | 382/128 |
| 7,656,999 B2* | 2/2010 | Hui | A61N 5/1084 |
| | | | 378/147 |
| 7,831,016 B2* | 11/2010 | Saoudi | A61N 5/1048 |
| | | | 378/65 |
| 2004/0001569 A1 | 1/2004 | Luo | |
| 2007/0286331 A1 | 12/2007 | Keall et al. | |
| 2008/0081991 A1* | 4/2008 | West | A61N 5/1031 |
| | | | 600/425 |
| 2008/0144772 A1 | 6/2008 | Yi et al. | |
| 2009/0116616 A1* | 5/2009 | Lu | A61N 5/1049 |
| | | | 378/65 |
| 2010/0012829 A1 | 1/2010 | Islam et al. | |
| 2014/0005464 A1 | 1/2014 | Bharat et al. | |

\* cited by examiner

BEAM SEGMENT-LEVEL DOSE COMPUTATION AND TEMPORAL MOTION TRACKING FOR ADAPTIVE TREATMENT PLANNING

CROSS REFERENCE TO RELATED APPLICATIONS

This application is a national filing of PCT application Serial No. PCT/IB2012/056867, filed Nov. 30, 2012, published as WO 2013/080175 A1 on Jun. 6, 2013, which claims the benefit of U.S. provisional application Ser. No. 61/564,885 filed Nov. 30, 2011, which is incorporated herein by reference.

This invention was made with government support under grant CA134541 awarded by the National Institutes of Health. The government has certain rights in the invention.

The present application relates generally to external beam radiation therapy (EBRT). It finds particular application in conjunction with individual beam segment-level dose computation and temporal motion tracking for adaptive treatment planning in external beam radiation therapy, and will be described with particular reference thereto. However, it is to be understood that it also finds application in other usage scenarios, and is not necessarily limited to the aforementioned application.

In external beam radiation therapy (EBRT), spatially targeted doses of radiation are applied to tumors or other targets containing cancerous or malignant tissue. Growing and rapidly multiplying cancer cells tend to be more susceptible to damage from radiation, as compared with normal cells, such that dosages administrated by proper planning preferentially kill cancerous or malignant tissue. Traditionally, EBRT consists of three stages: simulation (imaging), planning, and delivery, in that order. The treatment planning is usually performed using Computed Tomography (CT) images obtained apriori. The radiation delivery is divided into one or more fractions delivered on a daily basis. Since the imaging, planning, and delivery stages are performed on different days, patient anatomy during radiation delivery may differ from that during imaging stage. This is due to various reasons such as weight loss, organ motion, tumor shrinkage, etc. In addition, breathing patterns, physiological changes, and random patient movement during radiation delivery can also alter the patient anatomy relative to the radiation beam.

To adapt original treatment plans and/or make inferences about the success of the plan delivery, clinics have started using feedback mechanisms (image-based and tracking-based) during treatment. The feedback mechanisms provide the ability to relate geometric changes in patient anatomy to the 3D dose distribution received by the patient. Image-based feedback routines (e.g. cone beam CT (CBCT), MVCT, B-mode Acquisition, Targeting (BAT) ultrasound, and the like) are utilized in between fractions and related to the CT simulation using deformable registration algorithms. Tracking-based methods (e.g. optical tracking, electromagnetic (EM) tracking, and the like) are also used during radiation delivery to obtain intrafraction motion information.

Existing methods for dose estimation/accumulation (e.g. dose convolution with motion) assume a stationary (time-invariant) plan dose distribution. In other words, when the spatial position of the target is related to the plan dose grid, it is assumed that the dose from all gantry angles and individual beam segments is delivered simultaneously. This assumption allows the cumulative dose from all beams (gantry angles) and beam segments to be used in dose convolution algorithms. This assumption is valid in a dosimetric sense for stationary and anatomically-invariant targets, which however, is rarely the case. Additionally, the treatment plan specifies a finite number of gantry angles (beams) and each beam has a finite number of segments or control points. These gantry angles and segments are accessed in a sequential manner.

The present application describes an algorithm of dose verification that allows the position of the target and/or surrounding normal tissue to be correlated with the actual dose being delivered at that instant without the assumption of dosimetric time-invariance in the dose estimation protocol. Thus, the accuracy of the estimated dose is improved, since organ motion during delivery is correlated directly with the dynamic delivered dose and not with the static plan dose.

The present application provides new and improved methods and systems which overcome the above-referenced problems and others.

In accordance with one aspect, a treatment planning system is provided. The system including one or more processors programmed to receive a radiation treatment plan (RTP) for irradiating a target over the course of one or more treatment fractions, said RTP including a planned dose distribution to be delivered to the target, receive motion data for at least one of the treatment fractions of the RTP, receive temporal delivery metric data for at least one of the treatment fractions of the RTP, calculate a motion-compensated dose distribution for the target using the motion data and the temporal delivery metric data to adjust the planned dose distribution based on the received motion data and temporal delivery metric data, and compare the motion-compensated dose distribution to the planned dose distribution.

In accordance with another aspect, a method for generating patient-specific treatment. The method including receiving a radiation treatment plan (RTP) for irradiating a target over the course of one or more treatment fractions, said RTP including a planned dose distribution for the target an other regions of interest (for each segment, beam, and the whole), receiving motion data for at least one of the treatment fractions of the RTP receiving temporal delivery metric data for at least one of the treatment fractions of the RTP, calculating a motion-compensated dose distribution for the target using the motion data and temporal delivery metric data to adjust the planned dose distribution based on the received motion data and temporal delivery metric data; and, comparing the motion-compensated dose distribution to the planned dose distribution.

One advantage resides in providing improved and more accurate dose estimation.

Another advantage resides in calculating a radiation dose actually delivered to a patient.

Another advantage resides in more accurate delivery of radiation to a target region.

Another advantage resides in more accurately determining a radiation dose actually delivered to target and non-target tissue.

Another advantage resides in improvement in radiotherapy treatment planning workflows used in medical institutions.

Another advantage resides in reducing the risk of normal tissue damage.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
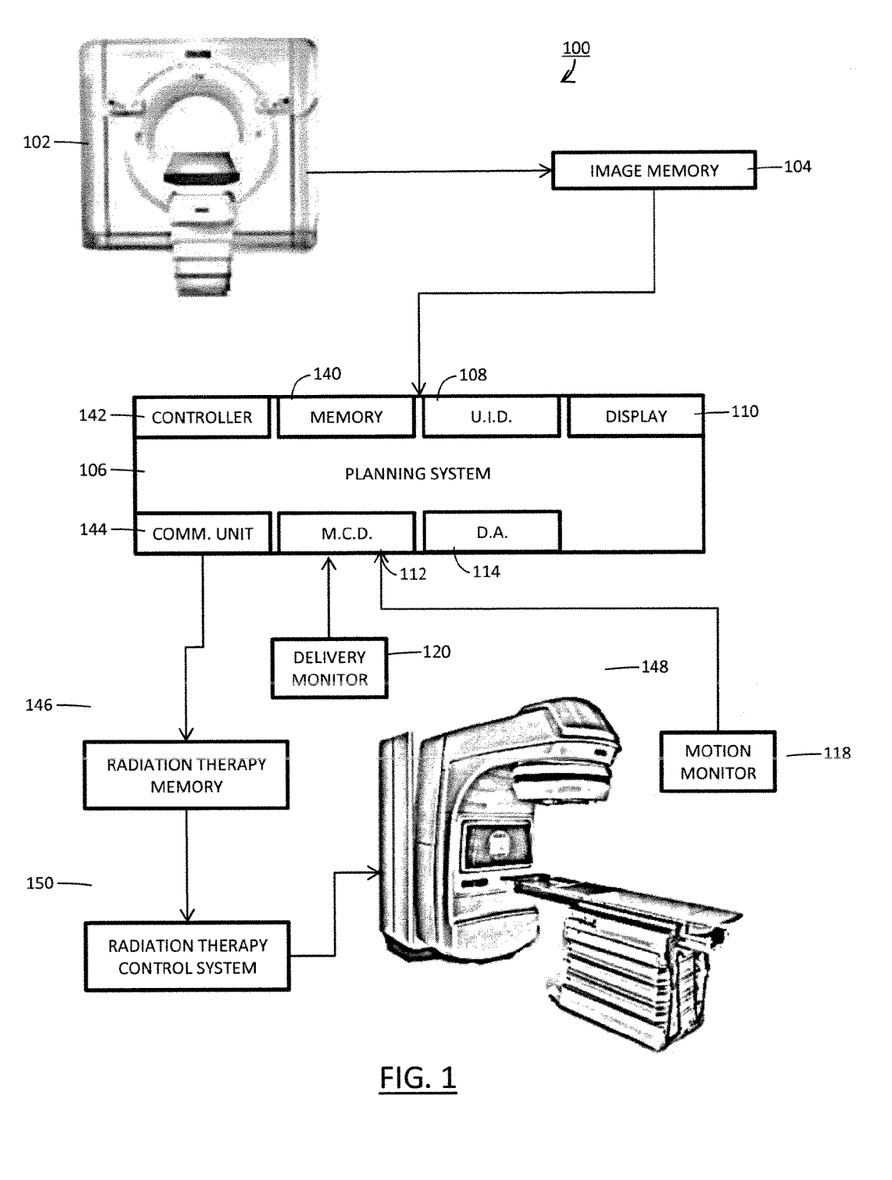
FIG. 1 is a radiation therapy system in accordance with aspects of the present disclosure.

FIG. 1 illustrates a radiation therapy system 100 for treating patients which implements a workflow that provides individual beam segment-level dose computation and temporal motion tracking for adaptive treatment planning. Typically, treatment plans for external beam radiation therapy (EBRT) are usually 'static', i.e. they are generally developed based on a single computed tomography (CT) scan. However, the patient's internal anatomy can exhibit varied motion during radiation delivery, which, if not accounted for, may lead to significant dosimetric errors. Also, the treatment plan describes a multi-beam dose distribution that is temporally invariant. However, radiation delivery is sequential, with each individual radiation beam delivered for a specific time only. Every beam also consists of one or more segments, each of which irradiates a specific region of the target. The workflow, as described below, improves the accuracy of estimating the effect of motion on dose, based on high temporal frequency tracking information on target motion and machine delivery status. The dose computed from each individual segment of each beam is correlated with the tracked position of the target, to estimate the dose actually received by the target and/or surrounding normal tissue. This information can be used in adaptive treatment planning/autoplanning workflows.

With reference to FIG. 1, the radiation therapy system is employed to provide radiation therapy to a patient, such as one or more of external beam radiation therapy, proton therapy, ablation therapy and high-intensity focused ultrasound therapy. The radiation therapy system 100 includes one or more imaging modalities 102 suitable for acquiring images embodying objects of interest (OOIs), such as regions of interest (ROIs) and points of interest (POIs), within the patients. The imaging modalities 102 suitably include a computed tomography (CT) scanner. However, the imaging modalities 102 can additionally or alternatively include one or more of a positron emission tomography (PET) scanner, a magnetic resonance (MR) scanner, a single photon emission computed tomography (SPECT) scanner, and the like.

Images acquired from the imaging modalities 102 are typically three-dimensional images. However, two-dimensional images are contemplated. Three-dimensional images typically include a stack of two-dimensional images, hereafter referred to as slices. Further, images acquired from the imaging modalities 102 are stored in an image memory 104. Typically, the image memory 104 is a central records storage system. However, it is contemplated that the image memory 104 is local to the imaging modalities 102 or another component of the radiation therapy system 100. Insofar as the image memory 104 is remote from the imaging modalities 102, the imaging modalities 102 are suitably connected therewith via a communications network, such as a local area network (LAN).

A planning system 106 of the radiation therapy system 100 receives planning images for each of the patients and employs the images to generate and/or update radiation therapy treatment plans (RTPs) and/or to perform post-treatment analysis of RTPs. A planning image is an image used to generate and/or update an RTP. Typically, the images are acquired from the image memory 104 and/or the imaging modalities 102. However, the images can be acquired from other sources. Further, the planning images are typically received electronically via a communications network. However, other means of receiving the planning images are contemplated. Suitably, the planning system 106 provides typical treatment planning functionalities, such as manual and automated segmentation tools, image fusion tools, three-dimensional conformal radiotherapy (CRT) planning tools, inverse intensity-modulated radiation therapy (IMRT) optimization tools, dose calculation tools, and so on.

To generate an RTP for a patient, the planning system 106 receives one or more planning images before radiation therapy. The planning images are suitably focused on one or more tumors or other targets of the patient to be treated or observed. Further, the planning images are suitably three-dimensional and include a plurality of slices (or two-dimensional images).

Upon receiving the planning images, a contour (or trajectory) is identified around each of the tumors or other targets and one or more organs at risk (OARs) or other regions. Contouring is used to delineate between the tumors or other targets and the OARs or other regions and between the OARs and the other regions. An oncologist or other clinician suitably performs the contouring. However, automated and semi-automated approaches are contemplated. Insofar as a clinician performs or asserts the contouring, the clinician suitably employs one or more user input devices 108 to identify the contours on a graphical user interface presented via a display 110. For example, the graphical user interface can display a planning image and allow the clinician to draw or mark the contours on the planning image using the user input devices 108.

In addition to identifying the contours, radiation plan parameters are defined for the contoured regions. Suitably, the clinician or oncologist defines the radiation plan parameters via the graphical user interface. For example, the clinician defines the radiation plan parameters using the user input devices 108. However, as with contouring, automated approaches are contemplated. The radiation plan parameters typically include minimum or target doses to be delivered to the tumors or other targets, maximum permissible doses for the OARs or other regions, and the like.

The radiation therapy plan parameters, together with known information about radiation attenuation or absorption characteristics of the various tissues and the contoured tumors or other targets and the contoured OARs or other regions, are used to generate the RTP. As discussed below, the RTP defines trajectories along which the radiation beams irradiate the targets, the radiation beam spatial projection of each radiation beam trajectory, the intensity of the radiation beam along each trajectory, the duration the targets are irradiated along each trajectory, or the like. In certain embodiments, the RTP is optimized for the particular type of radiation therapy, such as external beam radiation therapy, proton therapy, ablation therapy and high-intensity focused ultrasound therapy.

During each radiation therapy session, the cumulative dose of radiation delivered to tumors or other targets and OARs or other regions is determined. As the therapy session progress, the tumors or other targets typically shrink and the OARs or other regions typically shift, potentially causing errors in the accumulated dose calculations and the contours (or trajectories). The RTP and the integration of cumulative radiation dose delivered to the tumors or other targets and the OARs or other regions assumes the locations and sizes of the tumors or other targets and the OARs or other regions remain as is in the images on which the RTP is based. If these locations or sizes change, the cumulative radiation doses will have inaccuracies. Therefore, to maintain accuracy, the RTP is periodically updated. Although RTPs are typically updated between treatment fractions, it is contemplated that RTPs are updated during treatment fractions, other predetermined time periods, continuously, and the like.

For example, during the radiation therapy session, the dose is delivered using multiple gantry angles (one at a time). The fluence emanating from each gantry angle is referred to as a beam. Each beam consists of multiple segments, which correspond to different arrangements of the multileaf collimator (MLC) leaf positions. Each segment may be tailored to irradiate a particular region of the target. Traditional dose computation schemes cumulatively add the dose from each segment of every beam together, to arrive at the final dose distribution. The workflow, as described below, computes and stores the dose from each segment of every beam separately, in addition to the cumulative dose grid. Specifically, the dose distribution may be broken down into its constituent components on the basis of additional or other factors, such as (but not limited to) MLC leaf motion patterns, leaf velocities, gantry path, angular velocity etc.

To update an RTP for a patient, the planning system 106 typically receives one or more new planning images. For example, the planning system 106 receives planning images after each, or a predetermined number of, radiation therapy sessions (or fractions). As above, the planning images are suitably focused on one or more tumors or other targets of the patient. Upon receiving a new planning image, or upon receiving a predetermined number of new planning images, the contours (or trajectories) and/or the doses of the RTP are typically updated through comparison of the new planning images to the planning images used to generate the RTP and/or previous fractions. Additionally or alternatively, in certain embodiments, the RTP is updated using a motion/delivery compensated dose module 112 and dosimetric analysis module 114 of the planning system 106.

The motion/delivery compensated dose module 112 calculates doses actually delivered to a patient (hereafter referred to as motion-compensated dose distributions) during one or more fractions of an RTP based on motion data of a patient collected during and/or between the fractions and the temporal delivery metrics collected from each beam/segment at different time instants of the radiation delivery. A motion monitor 118 generates motion data indicative of motion of the tumors or other targets and/or the OARs or other regions, relative to previous fractions and/or the RTP. In that regard, the motion data is typically defined in the coordinate frame of the planning images employed to generate the previous fraction and/or the RTP. A dose delivery monitor 120 generates temporal delivery metric data indicative of the temporal delivery metrics received from a treatment delivery apparatus, such as a linear accelerator (LINAC), of a radiation therapy apparatus which details the status of each beam/segment at each time instant of radiation delivery. Additionally, the motion/delivery compensated dose module 112 relates the positional information of the target/surrounding normal tissue during treatment to the specific component of the plan dose distribution using the temporal delivery metric data and utilizes this relationship to calculate the dose actually delivered to the patient.

The motion data is typically received from one or more surrogates for the tumors, targets, or other organs (hereafter referred to as target surrogates). For example, the motion data is received from three target surrogates disposed at different locations within the patient. In certain embodiments, the target surrogates are RF transponders disposed closely adjacent to the target. The motion monitor 118 in one embodiment includes radio receivers at each of a plurality of surrounding locations which monitor the signals from the transponders for phase shifts or other indicators of displacement and triangulate the location of each transponder. From the spatial relationship between the transponders and the target, indicated in the most recent planning images, displacement or a change in shape of the targets is determined. In other embodiments, the target surrogates are fiducial markers implanted in the patient. In one embodiment, the motion monitor 118 includes an imaging device, such as ultrasounds imaging, projection x-ray imaging, magnetic resonance imaging (MRI), CT imaging, or the like, operating, for example, in a fluoroscopic mode. Displacement of the fiducials is determined by analyzing the fluoroscopic images. In certain embodiments, target surrogates are not employed. Rather, image-based motion tracking is employed to receive the motion data. In one embodiment, the motion monitor 118 includes an imaging device, as above, that facilitates image-based motion tracking of the target in real-time using, for example, contours or anatomical structures.

The motion data can be received continuously, on-demand, upon the occurrence of an event, such as a timer event, and so on, but is typically received periodically during radiation therapy, such as at a frequency of 10 Hz. Where the motion data is received continuously, it is suitably broken into discrete blocks based on time and a trending algorithm, such as minimum, median, maximum, mean, and so on, is applied to the discrete blocks.

The temporal delivery metric data is typically received from the dose delivery monitor 120 which details the status of each beam/segment at different time instants of radiation delivery such as the radiation delivery pattern and sequencing. The temporal delivery metric data includes the angular position of the gantry at all times during that fraction in small time increments such as 10-50 ms, although any frequency can be used, the number of the control points or segments belonging to a particular beam that is active at any given time instant, and the like. The temporal delivery metric data can be received continuously, on-demand, upon the occurrence of an event, and so on, but is typically received periodically during radiation therapy setup and delivery.

Contemporaneous with or after motion data is collected, the motion/delivery compensated dose module 112 utilizes the motion data from the target and/or surrounding normal tissue and the temporal delivery metric data to calculate motion compensated dose distributions. Specifically, the motion/delivery compensated dose module 112 correlates the motion data indicative of motion of the tumors or other targets and/or the OARs or other regions at each time step to the temporal delivery metric data indicative of the temporal delivery metrics received from the treatment delivery apparatus, such as the LINAC.

In certain embodiments, this includes, for each time step (or sample) of collected motion data, estimating rigid or deformable motion of the target surrogates relative to the most recent planning image used to generate the RTP for the fraction associated with the time step. For example, suppose motion data for three target surrogates is collected over the course of two treatment fractions. A motion estimate is determined for the target and cuticle tissues relative to the most recent planning image used for the first fraction. The motion estimate shows the range of locations over which the target moved and frequency with which the target was in each location. Rigid motion components include translations and rotations. Non-rigid motion can also be employed.

After determining the motion estimates, a cumulative motion pattern for the tumor or other target during at least a portion of a fraction is determined. Specifically, each of the motion estimates corresponding to a given combination of the active segment and beam are grouped together. Thus, for each active segment belonging to a particular beam, there is a group of motion estimates that correspond to the motion that the target underwent at those time instants. The motion estimates from each are then grouped to all the target voxels and one or more probability density functions (PDFs) are created for each of the tumors or other targets based on the motion estimates for each group. These PDFs represent the motion patterns of the target during each active segment-beam combination.

The PDF or other deterioration model is created by applying each of the motion estimates and corresponding temporal delivery metric data associated with the treatment fraction to the tumor or other target to yield a motion-compensated location. The motion of the tumor or other target and temporal delivery metric data are accumulated into a PDF to determine the cumulative motion pattern of the tumor or other target during the fraction. Application of a motion estimate to a tumor or other target and temporal delivery metric data shows a portion of the time during irradiation with the treatment beam that the target was all or partially out of the treatment beam and which portions were out for how long.

For each of the PDFs, the planned dose distribution corresponding to the PDF is convolved with the PDF to determine a motion compensated dose distribution for the fraction(s) corresponding to the PDF. Specifically, the dose grids are convolved with the appropriate group of PDFs to generate the motion compensated dose grid components. The final motion compensated dose distribution is calculated by adding all the motion-compensated dose grids. The motion compensated dose distributions for a tumor or other target can be accumulated until the end of a portion (or subset) of a fraction, one fraction, or a subset of the fractions.

Alternatively, the motion of each sample or some down samples of the motion data can be applied directly to the position of the dose distribution to create a motion compensated dose distribution. The motion compensated dose distribution can be weighted based on the amount of time the samples represents and summed to create a composite motion compensated dose distribution.

The dosimetric analysis module 114 compares the motion compensated dose distributions of the tumors or other targets to corresponding planned dose distributions qualitatively or quantitatively. Typically, but not necessarily, the motion compensated dose distributions are received from the motion/delivery compensated dose module 112. In certain embodiments, if significant dosimetric deviations from the planned dose distributions are detected, imaging is performed using the imaging modalities 102 as a reality check on the motion compensated dose distributions.

To qualitatively compare a motion compensated dose distribution of a tumor or other target with the planned dose distribution, the motion compensated dose distribution and the planned dose distribution are graphically displayed on a graphical user interface presented to an oncologist or other clinician via the display 110. In certain embodiments, the dose distributions are displayed adjacent to one another, such as side-by-side. In other embodiments, the dose distributions are displayed overlaid on one another with varying transparencies. Suitably, color is employed to identify dose intensity. For example, a gradient is employed to identify relative intensity, where the darker the color the greater the intensity. Further, the contours (or trajectories) can be overlaid thereon. Using the user input devices 108, the clinician can sequentially advance through the slices in any dimension (e.g., transverse, sagittal, coronal, oblique, etc.) and observe the resulting two-dimensional dose distributions for a slice. Slices or projections transverse to one or more therapy beam trajectories are contemplated. Advantageously, this can help identify obvious and/or large-scale differences in dose and their spatial locations. In other words, this can help identify hot spots and/or cold spots. A hot spot is an area where more radiation than expected was received, and a cold spot is an area where less radiation than expected was received. In certain embodiments, the qualitative comparison further includes receiving comparison data from the user input devices 108, the comparison data indicating dosimetric differences between the dose distributions, such as the degree of similarity of the dose distributions, the location of hot spots and/or cold spots, and so on.

To quantitatively compare the dose distributions, a number of different approaches are contemplated. In certain embodiments, a difference between a planned dose distribution and a motion compensated dose distribution is calculated. The difference provides information regarding the presence of cold spots (or hot spots) in terms of at least one of magnitude, location and extent. Thresholds can, for example, be applied to the difference to identify cold spots and/or hot spots. Additionally or alternatively, in certain embodiments, one or more of dose volume histograms (DVHs), maximum doses, mean doses, minimum doses, dose at user specified volumes, etc. of both dose distributions are compared. Thresholds can, for example, be applied to the comparison to simplify the identity of clinically significant differences. Additionally or alternatively, in certain embodiments, the dosimetric impact of motion is quantified as a weighted combination of the above factors, with the weights decided by an oncologist or other clinician.

To perform a post-treatment analysis of an RTP, the planning system 106 receives one or more images after the RTP has completed and/or motion data, as described above. The images are suitably focused on one or more tumors or other targets of the patient. Upon receiving the new images and/or the motion data, at least one of the motion/delivery compensated dose module 112 and the dosimetric analysis module 114 is employed to analyze the RTP. The motion corrected cumulative dose values are determined. The RTP is adjusted in accordance with the new image, the cumulative dose, the motion model, and the like. For example, the dosimetric analysis module 114 can be used to study the effect of motion on the RTP.

The planning system 106 suitably includes one or more memories 140 and one or more processor-based controllers 142. The memories 140 store executable instructions for controlling a processor of the processor-based controllers 142 to perform one or more of the above noted functions of the planning system 106. Further, in certain embodiments, at least one of the motion/delivery compensated dose module 112 and the dosimetric analysis module 114 is embodied by executable instructions stored in, for example, the memories 140. The processor-based controllers 142 execute the executable instructions stored on the memories 140 to carry out the functions associated with the planning system 106.

Where the planning system 106 is operative to perform at least one of receive images from a communications network, store RTPs over a communications network, and receive motion data from a communications network, the planning system 106 further includes one or more communications units 144 facilitating communication between the processor-based controllers 142 and the communications networks.

The RTPs generated and/or updated by the planning system 106 are stored in a radiation therapy plan memory 146. Typically, the radiation therapy plan memory 146 is the central records storage system. However, it is contemplated that the radiation therapy plan memory 146 is local to the planning system 106 or another component of the radiation therapy system 100. Insofar as the radiation therapy plan memory 146 is remote from the planning system 106, the radiation therapy plan memory 146 is suitably connected therewith via a communications network, such as a local area network (LAN).

At a scheduled day and time for a radiation therapy session or fraction of an RTP, a radiation therapy apparatus 148 is employed to deliver therapeutic radiation to the patient. The radiation can include gamma rays, particles, x-rays, protons, heat, sound, and so on suitable for radiation therapy, such as external beam radiation therapy, proton therapy, ablation therapy and high-intensity focused ultrasound therapy. Suitably, the radiation therapy apparatus 148 is controlled by a radiation therapy control system 150 in accordance with the RTP stored in the radiation therapy plan memory 146. For example, in the illustrated embodiment, the radiation therapy delivery apparatus 148 includes the linear accelerator (LINAC), and the radiation therapy control system 150 operates multi-leaf collimator (MLC) or other radiation beam profile-shaping apparatus of the LINAC to modulate beam intensity and profile as the linear accelerator is moved or stepped around the subject, so as to deliver a radiation dose distribution into the subject that provides the desired integrated radiation dosage to the target feature while suitably limiting or constraining radiation exposure of sensitive critical features in accordance with the RTP.

Figure 2:
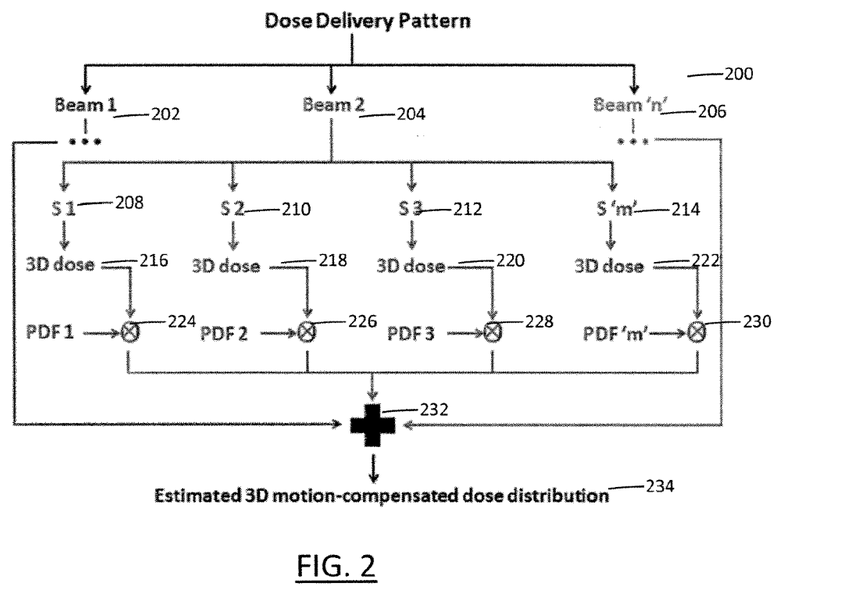
FIG. 2 depicts a dose delivery pattern according to aspects of the present disclosure.

With reference to FIG. 2, a block diagram of a dose delivery pattern is provided. The dose delivery pattern 200 includes a plurality of radiation beams 202, 204, 206. Each of the illustrated beams 202, 204, 206 represents all parameters pertaining to the particular beam. Each of the beams 202, 204, 206 consists of one or more segments 208, 210, 212, 214 and each of the segments has a dose distribution 216, 218, 220, 222 and motion PDF 224, 226, 228, 230 associated with it. As illustrated, the entire structure is only elaborated for Beam 2 but it is contemplated that Beam 1 and Beam 'n' would have similar structures. The estimated dose grids are added together 232 to generate the final motion-contemplated dose distribution 234.

Figure 3:
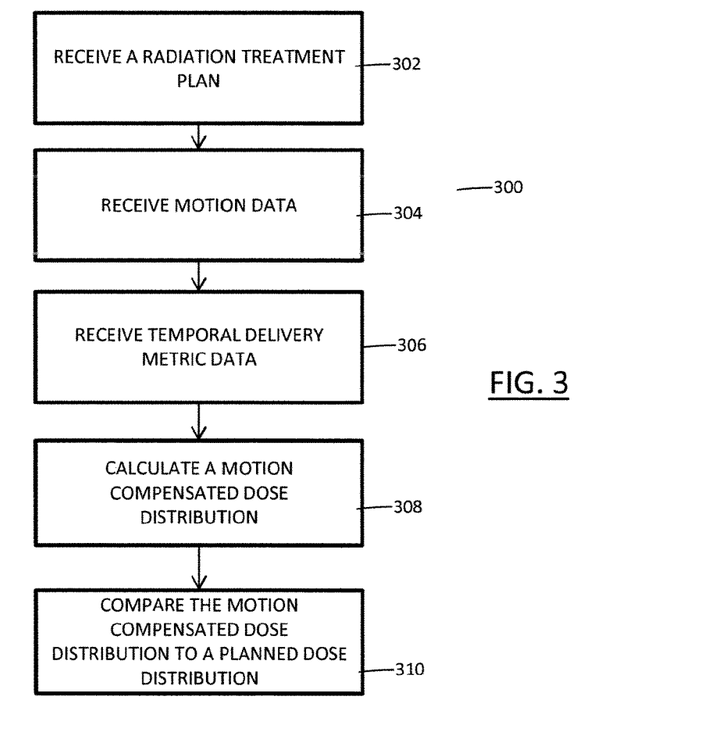
FIG. 3 depicts a method for generating patient-specific treatment according to aspects of the present disclosure.

With reference to FIG. 3, a block diagram of a method 300 performed by one or more processors to generate patient-specific treatment is provided. A radiation treatment plan (RTP) for irradiating a target over the course of one or more treatment fractions is generated or received 302. The RTP includes a planned dose distribution for the target. During at least one of the treatment fractions, motion data is received 304. Additionally, during at least one of the treatment fractions, temporal delivery metric data is received 306. A motion-compensated dose distribution for the target is calculated 308 using the motion data and temporal delivery metric data and the planned dose distribution. The motion-compensated dose distribution for the target utilizing the motion data and temporal delivery metric data to adjust the planned dose distribution based on the received motion data and temporal delivery metric data. Once the motion-compensated dose distribution is calculated, it is compared 310 to the planned dose distribution.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor-based controller includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A radiation therapy treatment planning system, comprising:
   one or more processors; and
   a non-transitory storage medium storing executable instructions programming the one or more processors to:
      receive a radiation treatment plan (RTP) for irradiating a target over a course of one or more treatment fractions, said RTP including a planned dose distribution to be delivered to the target;
      receive motion data of at least a part of a patient for at least one of the treatment fractions of the RTP performed by a treatment delivery apparatus and temporal delivery metric data received from the treatment delivery apparatus which details the status of each segment of each beam at each time instant of radiation delivery;
      receive temporal delivery metric data for at least one of the treatment fractions of the RTP;
      generate estimated dose grids for each beam from the motion data and the temporal delivery metric data;
      calculate a motion-compensated dose distribution for the target by summing each of the estimated dose grids;
      compare the motion-compensated dose distribution to the planned dose distribution;
      adjust the planned dose distribution based on the comparison to generate an adjusted RTP including the adjusted planned dose distribution; and
      store the adjusted RTP in a radiation therapy plan memory for use in controlling a radiation therapy apparatus to deliver the adjusted planned dose distribution to the target.

2. The radiation therapy treatment planning system according to claim 1, wherein the temporal delivery metric data includes at least one angular position of a gantry at all times during that fraction and a number of segments belonging to a particular beam that is active at any given time instant.

3. The radiation therapy treatment planning system according to claim 1, wherein the one or more processors are further programmed by the executable instructions stored on the non-transitory storage medium to:
optimize the RTP for one of external beam radiation therapy, proton therapy, ablation therapy and high-intensity focused ultrasound therapy.

4. The radiation therapy treatment planning system according to claim 1, wherein the one or more processors are further programmed by the executable instructions stored on the non-transitory storage medium to:
calculate the planned dose distribution from each segment of the beam; and
correlate the calculated planned dose distribution with the motion data to estimate the motion-compensated dose distribution received by the target.

5. The radiation therapy treatment planning system according to claim 1, wherein the one or more processors are further programmed by the executable instructions stored on the non-transitory storage medium to:
control a radiation therapy device comprising a linear accelerator by operating a multi-leaf collimator of the linear accelerator to perform beam modulation as the linear accelerator is moved or stepped in accordance with the adjusted RTP stored in the radiation therapy plan memory to deliver the adjusted planned dose distribution to the target.

6. The radiation therapy treatment planning system according to claim 5, wherein the one or more processors are further programmed by the executable instructions stored on the non-transitory storage medium to perform the adjusting after one or more treatment fractions.

7. The radiation therapy treatment planning system according to claim 5, wherein the one or more processors are further programmed by the executable instructions stored on the non-transitory storage medium to perform the adjusting during a fraction.

8. The radiation therapy treatment planning system according to claim 1, wherein the one or more processors are further programmed by the executable instructions stored on the non-transitory storage medium to calculate a motion-compensated dose distribution for the target using the motion data and the temporal delivery metric data by:
creating one or more probability density functions (PDFs) from the motion data and temporal delivery metric data, each of said PDFs representing a cumulative motion and delivery pattern of a target or an organ during one or more treatment fractions or any other period that motion data is collected.

9. The radiation therapy treatment planning system according to claim 8, wherein the one or more processors are further programmed by the executable instructions stored on the non-transitory storage medium to calculate the motion-compensated dose distribution for the target by:
convolving the planned dose distributions with the PDFs to determine the estimated dose grids indicative of a dose actually delivered to the target.

10. The radiation therapy treatment planning system according to claim 1, further including:
a display;
wherein the one or more processors are further programmed by the executable instructions stored on the non-transitory storage medium to compare the motion-compensated dose distribution to the planned dose distribution by at least one of:
displaying the motion-compensated dose distribution adjacent to the planned dose distribution on the display; and,
displaying the motion-compensated dose distribution overlaid on the planned dose distribution.

11. A radiation therapy system comprising:
one or more imaging modalities, comprising at least one of a computed tomography (CT) scanner, a positron emission tomography (PET) scanner, a magnetic resonance (MR) scanner, or a single photon emission computed tomography (SPECT) scanner, that obtain one or more planning images, the planning images being diagnostic images of a region of a subject to be treated;
a radiation therapy treatment planning system according to claim 1 that generates a radiation treatment plan (RTP) for irradiating a target over a course of one or more treatment fractions from the obtained one or more planning images, said RTP including a planned dose distribution for the target;
a radiation therapy apparatus including a linear accelerator (LINAC) with a multi-leaf collimator configured to deliver radiation therapy in accordance with the RTP;
a dose delivery monitor generating the received temporal delivery metric data indicative of the temporal delivery metrics of the radiation therapy apparatus; and,
a motion monitor generating the motion data from target surrogates of the target;
wherein the one or more processors of the radiation therapy treatment planning system are further programmed by the executable instructions stored on the non-transitory storage medium of the radiation therapy treatment planning system to:
adjust the RTP based on the motion data; and
control the radiation therapy device to deliver the adjusted RTP to the patient by operating the multi-leaf collimator to perform beam modulation as the LINAC is moved or stepped.

12. A radiation therapy system comprising:
a radiation therapy apparatus comprising a linear accelerator (LINAC) with a multi-leaf collimator (MLC), the radiation therapy apparatus configured to deliver radiation therapy in accordance with a radiation treatment plan (RTP);
a motion monitor generating motion data from target surrogates of a target;
a dose delivery monitor generating temporal delivery metric data indicative of one or more temporal delivery metrics of the radiation therapy apparatus; and,
one or more processors programmed to:
receive the RTP for irradiating a target over a course of one or more treatment fractions, said RTP including a planned dose distribution for the target;
receive the motion data for at least one of the treatment fractions of the RTP;
receive the temporal delivery metric data for at least one of the treatment fractions of the RTP;
generate estimated dose grids for each beam from the motion data and the temporal delivery metric data;
calculate a motion-compensated dose distribution for the target by summing each of the generated dose grids;
compare the motion-compensated dose distribution to the planned dose distribution;

adjust the RTP based on the compared motion-compensated dose distribution to the planned dose distribution; and control the radiation therapy apparatus including operating the MLC to perform beam modulation as the LINAC is moved or stepped to deliver radiation according to the adjusted RTP.

13. A method for generating a radiation therapy treatment plan, said method comprising:

receiving a radiation treatment plan (RTP) for irradiating a target over a course of one or more treatment fractions, said RTP including a planned dose distribution for the target;

receiving motion data of at least a part of a patient for at least one of the treatment fractions of the RTP;

receiving temporal delivery metric data for at least one of the treatment fractions of the RTP;

generating estimated dose grids for each beam from the motion data and the temporal delivery metric data;

calculating a motion-compensated dose distribution for the target using the motion data and temporal delivery metric data to adjust the planned dose distribution by summing each of the generated dose grids; and, comparing the motion-compensated dose distribution to the planned dose distribution;

generating an adjusted RTP from the comparison between the motion-compensated dose distribution to the planned dose distribution;

storing the adjusted RTP in a radiation therapy plan memory; and controlling a radiation therapy device with the adjusted RTP.

14. The method according to claim 13, wherein the generating of the adjusted RTP includes:

adjusting the generated radiation treatment plan based on dosimetric differences between the motion-compensated dose distribution and the planned dose distribution.

15. The method according to claim 13, further including:

generating estimated dose grids for each beam from the motion data and temporal delivery metric data; and calculating the motion-compensated dose distributions by summing each of the estimated dose grids.

16. The method according to claim 13, wherein the calculating includes:

creating one or more probability density functions (PDFs) from the motion data and the temporal delivery metric data, each of said PDFs representing a cumulative motion pattern of a target or an organ during the one or more treatment fractions or any other period that the motion data is collected; and, convolving the planned dose distributions with the PDFs to determine one or more motion-compensated doses indicative of a dose actually delivered to the target.

17. The method according to claim 16, wherein the calculating further includes:

accumulating the motion-compensated doses of at least one of the treatment fractions.

18. The method according to claim 13, wherein the comparing includes at least one of:

displaying the motion-compensated dose distribution adjacent to the planned dose distribution;

displaying the motion-compensated dose distribution overlaid on the planned dose distribution; and, calculating a difference between the motion-compensated dose distribution and the planned dose distribution.

* * * * *